US012408966B2

(12) United States Patent
Truckai

(10) Patent No.: US 12,408,966 B2
(45) Date of Patent: Sep. 9, 2025

(54) SYSTEMS AND METHODS FOR TREATING PYRONIES DISEASE

(71) Applicant: Kemeny Healthcare Inc., San Jose, CA (US)

(72) Inventor: Csaba Truckai, Saratoga, CA (US)

(73) Assignee: Kemeny Healthcare Inc., San Jose, CA (US)

( * ) Notice: Subject to any disclaimer, the term of this patent is extended or adjusted under 35 U.S.C. 154(b) by 666 days.

(21) Appl. No.: 17/647,680

(22) Filed: Jan. 11, 2022

(65) Prior Publication Data

US 2022/0218401 A1 Jul. 14, 2022

Related U.S. Application Data

(60) Provisional application No. 63/136,034, filed on Jan. 11, 2021.

(51) Int. Cl.
| | |
|---|---|
| *A61B 34/10* | (2016.01) |
| *A61B 18/02* | (2006.01) |
| *A61B 17/00* | (2006.01) |
| *A61B 17/34* | (2006.01) |
| *A61B 18/00* | (2006.01) |
| *A61B 90/00* | (2016.01) |

(52) U.S. Cl.
CPC .............. *A61B 18/02* (2013.01); *A61B 34/10* (2016.02); *A61B 2017/00792* (2013.01); *A61B 2017/3413* (2013.01); *A61B 2018/00005* (2013.01); *A61B 2018/00315* (2013.01); *A61B 2018/00642* (2013.01); *A61B 2018/00714* (2013.01); *A61B 2018/00791* (2013.01); *A61B 2018/0293* (2013.01); *A61B 2034/105* (2016.02); *A61B 2090/378* (2016.02)

(58) Field of Classification Search
CPC ............... A61B 18/02; A61B 34/10; A61B 2017/00792; A61B 2017/3413; A61B 2018/00005; A61B 2018/00315; A61B 2018/00642; A61B 2018/00714; A61B 2018/00791; A61B 2018/0293; A61B 2018/00547; A61B 2034/105; A61B 2090/378; A61B 2090/0418; A61B 2090/0463
See application file for complete search history.

(56) References Cited

U.S. PATENT DOCUMENTS

| | | | | |
|---|---|---|---|---|
| 5,019,076 A | * | 5/1991 | Yamanashi | A61B 18/082 606/49 |
| 2001/0007940 A1 | * | 7/2001 | Tu | A61B 18/1492 606/41 |
| 2002/0188286 A1 | * | 12/2002 | Quijano | A61B 18/02 606/41 |
| 2003/0014098 A1 | * | 1/2003 | Quijano | A61B 5/4381 607/122 |
| 2003/0199747 A1 | * | 10/2003 | Michlitsch | A61B 5/6853 600/407 |
| 2007/0213681 A1 | * | 9/2007 | Manna | A61B 17/22012 604/500 |
| 2020/0008871 A1 | * | 1/2020 | Teng | A61N 1/0551 |
| 2020/0398085 A1 | * | 12/2020 | Sullivan | G16H 50/30 |

\* cited by examiner

*Primary Examiner* — Ankit D Tejani
*Assistant Examiner* — Joshua Brendon Solomon
(74) *Attorney, Agent, or Firm* — Levine Bagade Han LLP

(57) ABSTRACT

Devices and methods, and for remodeling tissues to treat Peyronie's disease including devices and methods adapted for cryogenic cooling of targeted plaque in a male penis to selectively remodel targeted tissue.

20 Claims, 5 Drawing Sheets

SYSTEMS AND METHODS FOR TREATING PYRONIES DISEASE

CROSS-REFERENCE TO RELATED APPLICATIONS

This application claims benefit of priority to U.S. Provisional Patent Application No. 63/136,034 filed Jan. 11, 2021, the content of which is incorporated herein by reference in its entirety.

FIELD OF THE INVENTION

The present invention relates to medical devices and methods, and more particularly to cryotherapy devices for remodeling tissues to treat Peyronie's disease. Devices and methods of the invention are adapted for cryogenic cooling of targeted plaque in a male penis to selectively remodel such targeted tissue.

BACKGROUND OF THE INVENTION

Peyronie's disease is a condition resulting from fibrous scar penile tissue that causes curved, painful erections. Peyronie's disease causes a significant bend or pain in some men and can interfere or prevent maintaining an erection leading to erectile dysfunction.

Typically, Peyronie's disease does not go away on its own. In most men having Peyronie's disease, the condition remains or worsens.

SUMMARY OF THE INVENTION

The techniques described herein relate to methods for cryogenically treating Peyronie's disease, including providing a cryogenic device including at least one tissue-penetrating needle with a cooling tip; advancing the cooling tip into plaque in a subject's penile shaft; and cooling the plaque with the cooling tip thereby inducing a cooling injury to the plaque to achieve a therapeutic effect.

The techniques described herein can relate to a method wherein cooling the plaque with the cooling tip maintains the cooling tip at a targeted cooling temperature for at least 5 seconds. This targeted cooling temperature can be lower than −10 degrees Celsius and, in some variations, is between −10 and −80 degrees Celsius.

In additional variations, the techniques described herein relate to a method wherein cooling the plaque with the cooling tip includes maintaining the cooling tip in a stationary position in the plaque. In additional variations, the therapeutic treatment allows the plaque to be absorbed by a body of a patient.

The treatments described herein can result in reduced penile curvature.

Variations of the method can include imaging the plaque to provide a 3-dimensional map of the plaque. For example, such imaging can include the use of an ultrasound device. In additional aspects, the techniques and methods described herein relate to imaging during advancing the cooling tip.

In some aspects, the techniques described herein relate to a method further including a controller operatively coupled to the cryogenic device and the ultrasound device. Additional variations include methods wherein the controller is configured to modulate cooling the plaque in response to imaging signals from the ultrasound device.

In additional variations, the methods and techniques described herein include a controller that is configured to (i) record a 3-dimensional map of the plaque provided by the ultrasound device, (ii) monitor location of one or more cooling tips within the plaque with the ultrasound device; and (iii) actuate the cryogenic device to cool the plaque; and (iv) terminate cooling with the cryogenic device in response imaging with the ultrasound device.

Variations of the systems and methods can include a warming system with at least one warming needle with a warming tip and introducing a warming tip into tissue adjacent to the plaque. In some aspects, the methods can further include warming an adjacent tissue with the warming tip to thereby prevent a cooling injury to the adjacent tissue.

The warming can be performed prior to cooling the plaque, contemporaneous with cooling the plaque, and/or after cooling the plaque.

Additionally, the warming tip can be operatively coupled to the controller, and the controller is configured to modulate warming the adjacent tissue. In addition, or as an alternative, the method can include modulating warming of the adjacent tissue in response to signals from a temperature sensor carried by the warming tip.

DETAILED DESCRIPTION OF THE INVENTION

Figure 1:
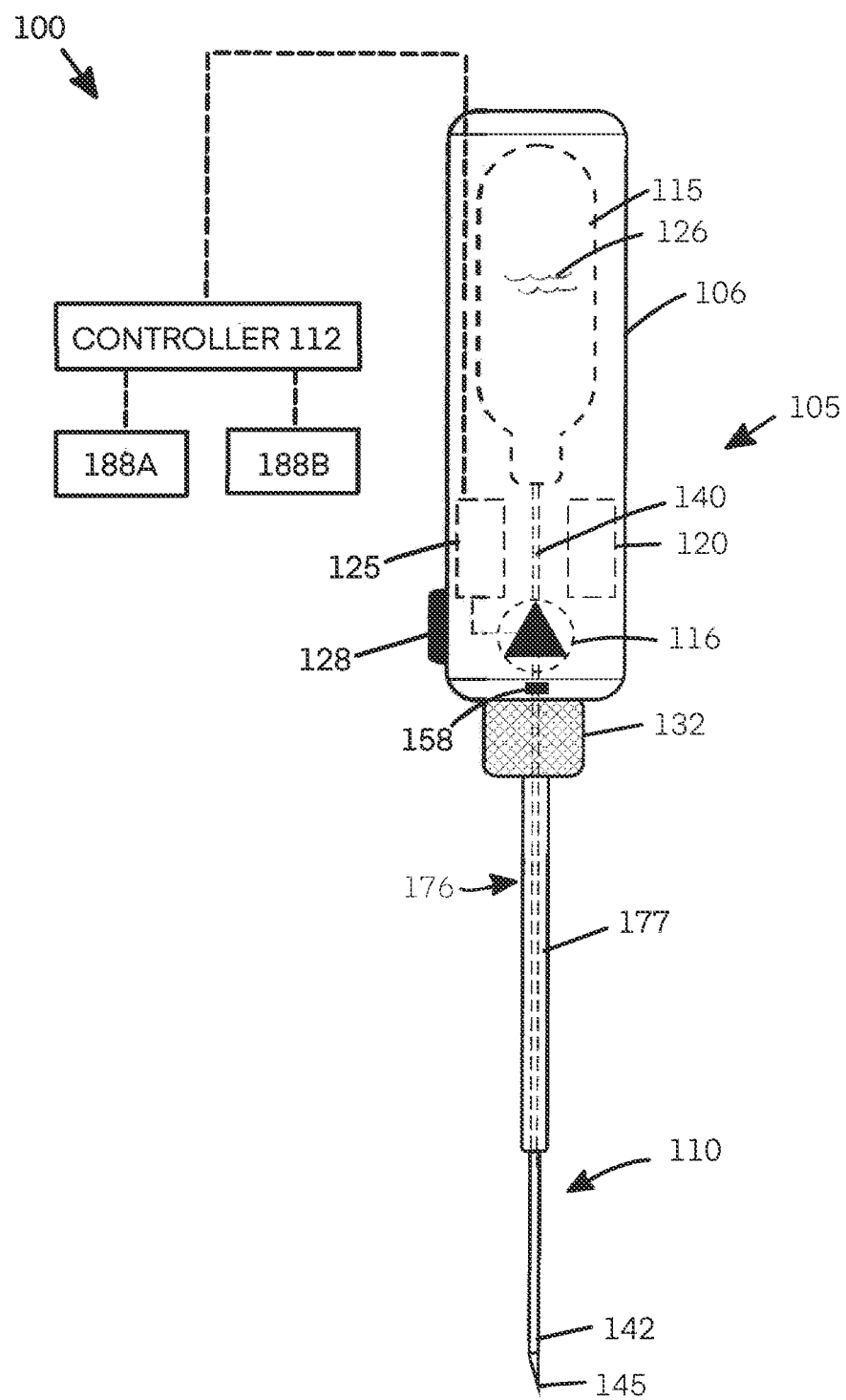
FIG. 1 is a schematic elevational view of a cryogenic probe and system corresponding to the invention with a needle assembly detachably coupled to a handpiece component together with an optional controller component.

Referring now to FIG. 1, a cryogenic treatment system 100 for cryogenic treatment of tissue is shown, which comprises a cryogenic probe 105 with a proximal handle or handpiece 106 coupled to a tissue-penetrating cryogenic needle 110. The handpiece 106 is adapted for gripping by human hand or can be configured for attachment to a robotic assembly as is known in the art. The cryogenic system optionally includes a controller 112 coupled to the probe 105 as will be described further below.

As shown in FIG. 1, a cryogenic cooling fluid assembly is carried within the handpiece 106, which typically consists of a single-use cooling cartridge 115 with and valve mechanism 116 operatively coupled to an electrical power source 120 adapted to open and close the valve mechanism 116. The electrical power source 120 further is coupled to a processor or subcontroller 125 for controlling flows of a cooling fluid 126 from the cartridge 115 to the tissue-penetrating needle 110. In one variation, the subcontroller 125 may be carried on a single processor board in the handpiece 106 and is adapted to perform one or more selected programs. The subcontroller 125 can comprise a programmable microprocessor that carries computer code or programming instructions for a treatment cycle, wherein such a treatment cycle typically comprises an on/off interval which delivers the cooling fluid 126 at a predetermined flow rate for a predetermined time interval which then provides a treatment of a predetermined volume a tissue which comprises the creation of an ice-ball in the targeted tissue or plaque as will be described below.

The power source 120 and valve mechanism 116 are typically activated manually by a switch 128 in the handpiece 106 that triggers the controller 125 to control a treatment cycle. The power source 120 can comprise a rechargeable battery or single-use battery that actuates, for example, a solenoid-type of valve mechanism 116.

Figure 2:
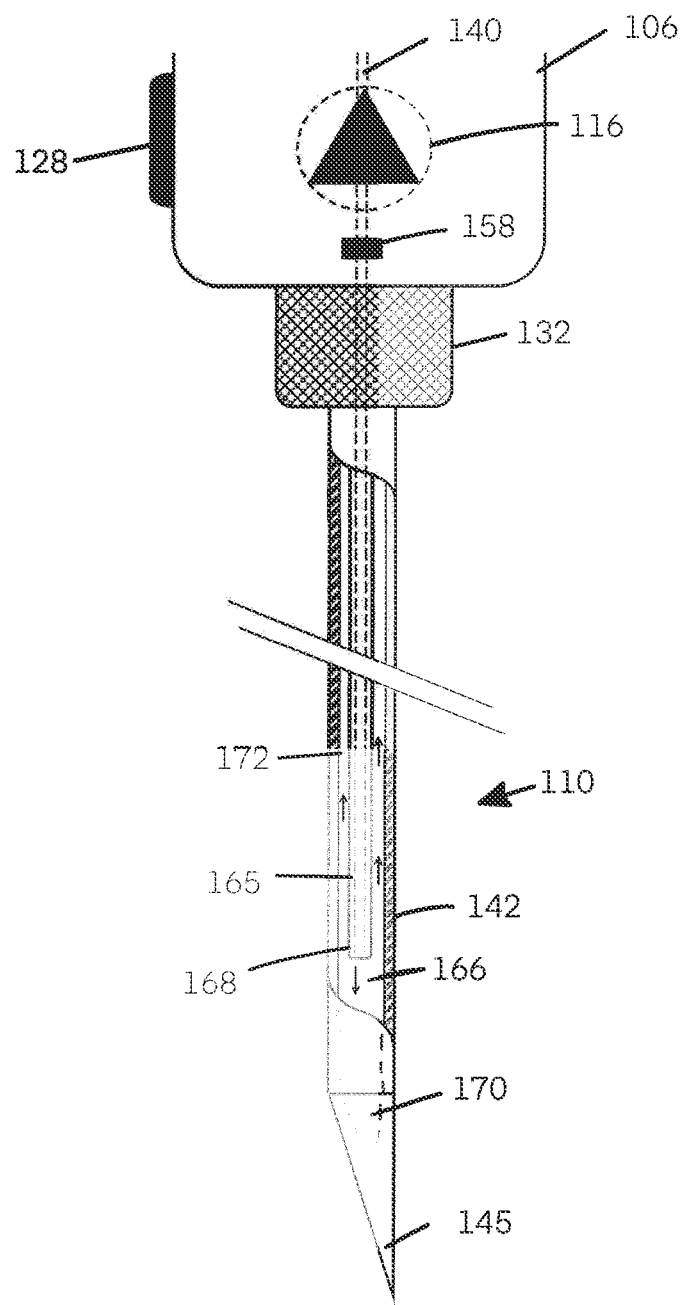
FIG. 2 is an enlarged cut-away schematic view of the cryogenic probe of FIG. 1, showing a cooling fluid injector tube in relation to the lumen in the needle.

Referring to FIGS. 1 and 2, in one variation, the cryogenic probe 105 carries a single hollow, tissue-penetrating needle 110 that may be detachably coupled to the handpiece 106 with coupling 132. A cooling fluid path 140 is shown in FIG. 1 that extends from cooling fluid source or cartridge 115 to the distal region 142 of the needle 110.

In a variation, still referring to FIGS. 1 and 2, the needle 110 can consist of a 30-gauge hollow hypotube having a sharpened, closed-end distal tip 145. The needle 110 can have any suitable axial length between the handpiece 106 and the distal tip 145 of the needle 110 ranging from 5 mm to 50 mm. Typically, the needle has a length from about 5 mm to about 20 mm although any length is possible. Such a needle 110 can be straight or have a curved distal portion. Such a needle 110 can comprise a stainless-steel material with an inner diameter of about 0.005" and an outer diameter of about 0.010" to 0.015". Alternative probes can carry multiple needles having other outer diameters from about 0.006 inches to about 0.100 inches (see FIG. 3). Typically, the needles will be a 16 gauge or smaller.

Figure 4:
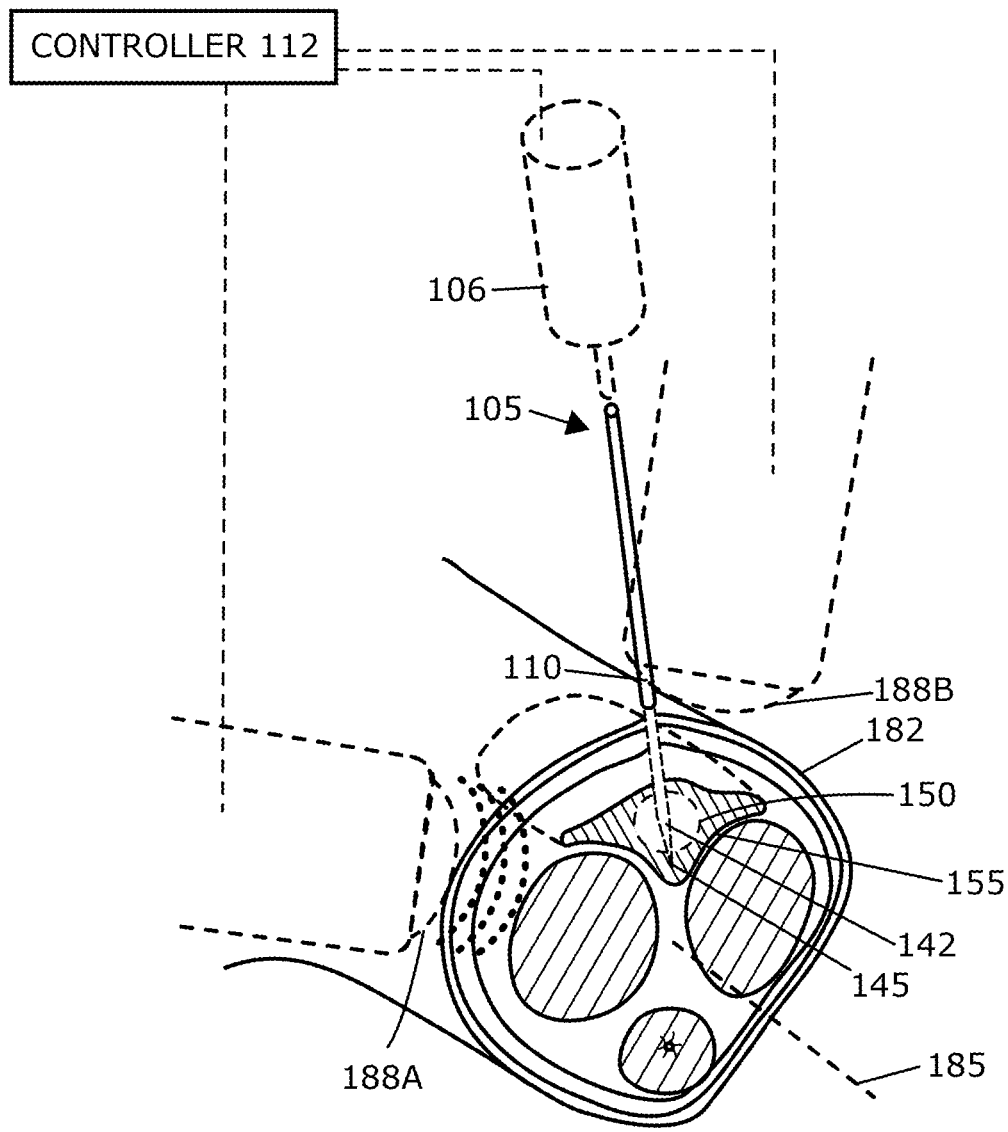
FIG. 4 illustrates a penile shaft of a subject with Peyronie's disease wherein the needle of the probe of FIG. 1 is shown after penetration into the plaque for providing cryogenic treatment together with ultrasound apparatus positioned to image the formation of an ice-ball in the plaque.

Referring to FIG. 1, in one variation, the exemplary cooling fluid supply or cartridge 115 contains a liquid cooling fluid 126 under high pressure, wherein the liquid preferably has a boiling temperature that is lower than body temperature (37° C.). Thus, when the cooling fluid 126 is delivered through the tissue-penetrating needle 110 when penetrated into targeted tissue, the heat from the targeted tissue will evaporate the liquid cooling fluid 126 within the needle 110, resulting in cooling the target tissue typically with the formation of an ice-ball 150 in the targeted tissue or plaque 155 (see FIG. 4). The valve 116 is provided within the handpiece 106 in the cooling fluid flow pathway 140 between the cartridge 115 and needle tip 145. Typically, the subcontroller 125 is configured to limit the cooling fluid flow rate and cooling fluid volume in a treatment cycle, which in turn controls the rate of temperature change the targeted tissue, and thereby controls the dimensions of the ice-ball 150 that is formed in the targeted tissue or plaque 155 (FIG. 4). The subcontroller 125 thus controls the pressure of the cooling fluid 126 delivered into the needle 110 and the temperature of the needle tip in contact the targeted tissue thus can be controlled. A mechanical pressure relief valve 156 also may be used to control the pressure within the lumen 158 of the needle 110 (FIG. 2).

In FIG. 1, the cooling fluid 126 is carried in a single-use cartridge 115 with a metal cap or seal, and in one variation, the cartridge contains liquid N2O. Other cooling fluids also can be used, where exemplary cooling fluids include fluorocarbon refrigerants and/or carbon dioxide. The volume of cooling fluid 126 contained by cartridge 115 typically is adequate to treat plaque 155 in a Peyronie's disease patient in a single procedure. An exemplary liquid N2O cartridge can contain, for example, a cooling fluid volume in a range of 10 grams to 100 grams of a cooling liquid.

Referring now to FIG. 2, the flow of cryogenic cooling fluid 126 from the cartridge 115 is controlled by the valve 116, which can comprise an electrically actuated solenoid valve or the like operating in response to control signals from the subcontroller 125 (FIG. 1). A typical valve 116 can be adapted for on/off operation and may provide for venting of the cooling fluid path downstream from the valve 116 after the valve is closed, which can limit residual cryogenic fluid vaporization and cooling.

In FIG. 2, the cryogenic cooling fluid 126 is released via valve 116 to flow through an injection tube 165 that communicates with the cooling fluid path 140 in the handpiece 106. The injection tube 165 is carried within the lumen 166 of the needle 110 and wherein the distal end 168 of the injection tube 165 extends close to the distal end 170 of the lumen 166 in the needle 110. The injection tube 165 can comprise a metal or polymer material or a combination thereof. The injection tube 165 has an outer diameter that is less than the diameter of the lumen 166 in the needle 110 such that outflows of a cooling fluid 126 (at least partly comprising a gas in the outflow) will be accommodated in the annular space 172 between the injection tube 165 and the wall of the needle 110. As an example, the injection tube 165 can have an inner lumen diameter ranging between 10 μm and 100 μm. An outer diameter of the injection tube 165 will typically be less than about 1000 and often being less than about 500 μm.

Figure 3:
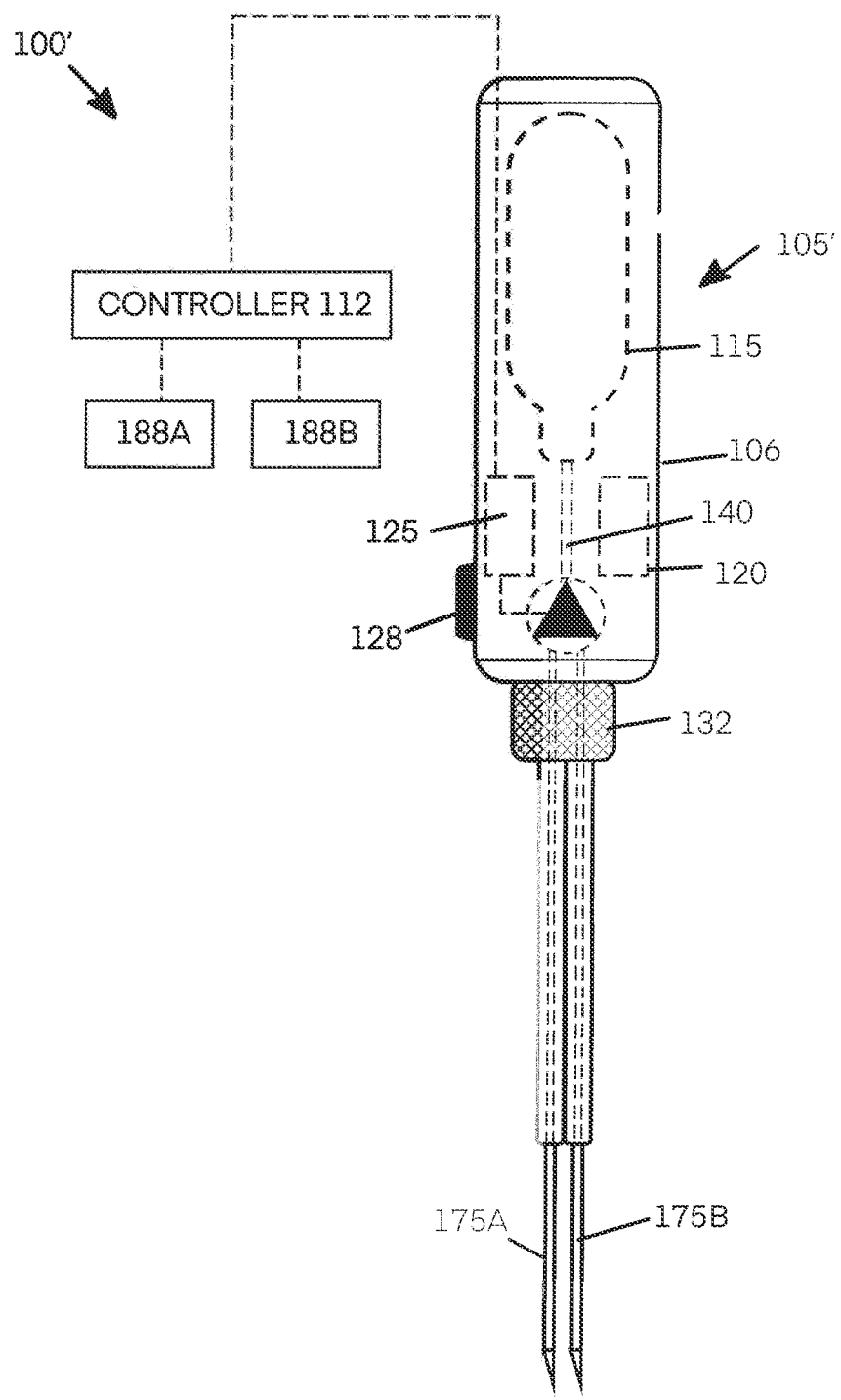
FIG. 3 is an illustration of a variation of the cryogenic probe of FIG. 1 with a needle assembly consisting of a plurality of tissue-penetrating needles.

Referring now to FIGS. 2 and 3, it can be understood that the cooling fluid 126 is injected into lumen 166 of needle 110 and as the liquid cooling fluid vaporizes within the needle 110, such vaporization will cool and freeze the tissue or plaque 155 in contact with the needle 110.

Referring now to FIG. 3, an alternative embodiment of a cryogenic system 100' and cryogenic probe 105' is shown that is similar to that of FIG. 1 except that the fluid path 140' from the cooling fluid cartridge 115 communicates with a plurality of needles and in this variation consist of two spaced-apart tissue-penetrating needles 175a and 175b. It should be appreciated that the number of such needles can range from 1 to 6 and operate as described above. In all other respects, the variation of FIG. 3 operates as described previously.

Referring back to FIGS. 1 and 2, the cartridge 115 can be initially inserted into the handpiece 106 and be adapted for use by piecing a metal cap of the cartridge 115 as is known in the art. Further, one or more filters (not shown) can be provided in the fluid path 140.

It should also be appreciated that the proximal portion 176 of the needle 110 (FIG. 1) can be supported and surrounded by an insulator member 177 adapted to limit heat transfer from the proximal portion 176 of the needle 110 to the environment. In other variation, the needle or needles can have flat or oval cross-sectional shapes which can be desirable for creating suitable ice-balls in tissue.

Referring now to FIG. 4, a method of treating Peyronie's disease is shown using the probe 105 of FIG. 1 where the objective is to cryogenically treat plaque 155 in a penile shaft 182 of the patient. In one method variation, the needle 110 is penetrated into the plaque 155 in an orientation that is generally perpendicular to the axis 185 of the penile shaft 182. In this variation, first and second ultrasound transducers 188A and 188B (also shown in FIG. 1) are positioned approximately 90° apart from another to provide for bi-planar views of the plaque 155 to optimally position the needle 110 in the plaque 155.

The ultrasound transducers 188A and 188B are subsequently used for observing the formation of the ice ball 150 in the plaque 155. During such a procedure, the physician would penetrate the needle 110 into the plaque 155 sequentially in multiple locations under ultrasonic monitoring and actuate the subcontroller 125 (FIG. 1) to deliver a predetermined cooling dose, which would be selected based on evaluation of the dimensions of the plaque prior to insertion of the needle 110. Following treatment, the patient would optionally tension the penile shaft 182 in a straightened position with traction devices that are known in the art. Within about two to six weeks following the procedure, the patient's immune system would absorb or resorb the treated plaque 155 and would reduce the volume of the plaque 155 in the range of 70% to 90%. With a reduction in the volume of the plaque 155, the penile shaft 182 would be straightened. The use of traction on the penile shaft 182 can be used for any suitable time interval post-treatment, for example, one to two weeks.

Figure 5:
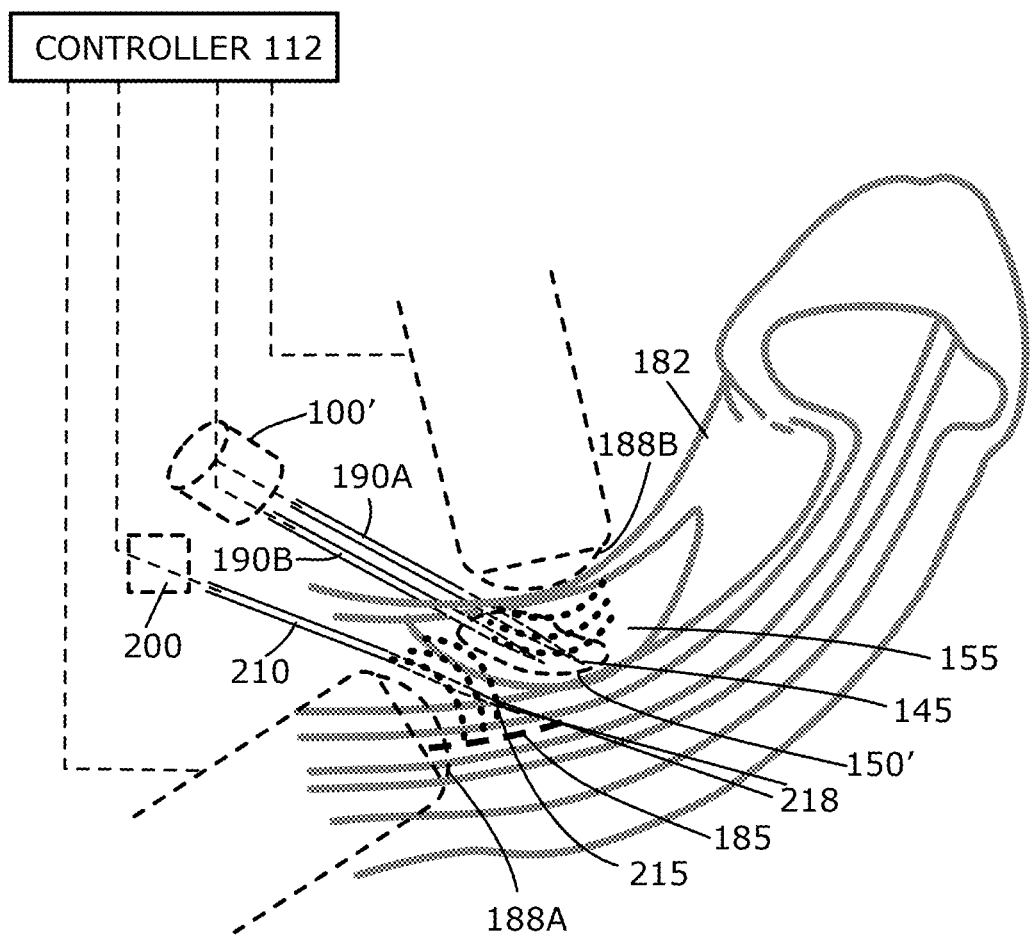
FIG. 5 is another view of a penile shaft with Peyronie's disease a probe with a plurality of cryogenic needles introduced into plaque in a penile shaft.

FIG. 5 illustrates another method of the invention for treating Peyronie's disease wherein the probe 100' has two needles 190a and 190b that are similar to the variation of FIG. 3. In the method shown in FIG. 5, it can be seen that the two needles 190a and 190b can be introduced from a lateral side of the plaque 155 rather than directly into the plaque from a superior position as shown in FIG. 4. In this case, dual ultrasound transducers 188A and 188B again can be positioned such that the needles 190a and 190b can be inserted into the plaque 155 prior to performing a treatment cycle. In this case, the dual needles 190a and 190b are adapted to create a more planar ice-ball 150' for ablating the plaque 155, which typically may form as a somewhat flat layer in the penile shaft 182.

In general, a method corresponding to the invention for cryogenically treating Peyronie's disease comprises providing a cryogenic device including at least one tissue-penetrating needle with a cooling tip, advancing the cooling tip into plaque in a subject's penile shaft, and cooling the plaque with the cooling tip thereby inducing a cooling injury to the plaque to achieve a therapeutic effect. Typically, the cooling step of the method maintains the cooling tip at a targeted cooling temperature for at least 5 seconds. The targeted cooling temperature is lower than −10 degrees Celsius and typically the temperature is between −10 degrees Celsius and −80 degrees Celsius.

In one variation, the cooling step of the method includes maintaining the cooling tip 145 in a stationary position in the plaque. Alternatively, the cooling step includes moving the cooling tip 145 in the plaque 155. Following the cooling step, the therapeutic result is achieved wherein the plaque is absorbed or resorbed by the patient's body and can reduce penile curvature.

In a variation, the method can include imaging the plaque to provide a 3-dimensional map of the plaque, typically with one or more ultrasound devices or transducers such as ultrasound transducers 188A and 188B shown in FIGS. 4 and 5. Such an imaging step can be used as the needle(s) and cooling tip 145 are advanced into the plaque 155 and during the cooling step to observe formation of the ice-ball 150 in the plaque 155.

In another variation of a treatment system and method, the system controller 112 is operatively coupled to the cryogenic probe 105 and the ultrasound devices or transducers 188A and 188B. In this variation, the system controller 112 is configured to modulate the cooling step in response to imaging signals from the ultrasound transducers 188A and 188B. Typically, the system controller 112 is configured to (i) record a 3-dimensional map of the plaque provided by the ultrasound system, (ii) monitor a location of one or more cooling tips within the plaque with the ultrasound system, (iii) actuate the cryogenic device to cool the plaque, and (iv) terminate cooling with the cryogenic device in response imaging with the ultrasound system.

In another variation, the treatment method further comprises the use of a tissue-warming system 200 with at least one warming needle 210 with a warming tip 215, wherein the warming tip 215 is introduced into tissue adjacent the plaque 155 to thereby prevent a cooling injury or freezing of such adjacent tissue. Such a method of warming tissue can be performed (i) prior to the step of cooling the plaque, (ii) contemporaneous with the step of cooling the plaque, and/or (iii) after the step of cooling the plaque. Such a warming system can be operatively coupled to the system controller 112 and such a controller can be configured to modulate the warming step. In one variation, the warming step is modulated in response to signals from a temperature sensor 218 carried by the warming tip 215 of the at least one warming needle 210.

What is claimed is:

1. A method for cryogenically treating Peyronie's disease, comprising:
   providing a cryogenic device including at least one tissue-penetrating needle with a cooling tip;
   advancing the cooling tip into plaque in a subject's penile shaft; and
   cooling the plaque with the cooling tip thereby inducing a cooling injury to the plaque to achieve a therapeutic effect by reducing curvature of the penile shaft.

2. The method of claim 1, wherein cooling the plaque with the cooling tip maintains the cooling tip at a targeted cooling temperature for at least 5 seconds.

3. The method of claim 2, wherein cooling the plaque with the cooling tip comprises cooling to a targeted cooling temperature lower than −10 degrees Celsius.

4. The method of claim 2, wherein the targeted cooling temperature is between −10 and −80 degrees Celsius.

5. The method of claim 1, wherein cooling the plaque with the cooling tip includes maintaining the cooling tip in a stationary position in the plaque.

6. The method of claim 1, wherein cooling the plaque includes moving the cooling tip in the plaque.

7. The method of claim 1, wherein the therapeutic effect comprises the plaque being absorbed by a body of a patient.

8. The method of claim 1, further comprising imaging the plaque to provide a 3-dimensional map of the plaque.

9. The method of claim 8, wherein imaging the plaque is performed with an ultrasound device.

10. The method of claim 8, further comprising imaging during advancing the cooling tip.

11. The method of claim 8, further comprising imaging during cooling the plaque.

12. The method of claim 8, further comprising imaging with an ultrasound device.

13. The method of claim 12, further comprising a controller operatively coupled to the cryogenic device and the ultrasound device.

14. The method of claim 13, wherein the controller is configured to modulate cooling the plaque in response to imaging signals from the ultrasound device.

15. The method of claim 14, wherein the controller is configured to (i) record a 3-dimensional map of the plaque provided by the ultrasound device, (ii) monitor location of one or more cooling tips within the plaque with the ultrasound device; and (iii) actuate the cryogenic device to cool the plaque; and (iv) terminate cooling with the cryogenic device in response imaging with the ultrasound device.

16. The method of claim 15, further comprising a warming system with at least one warming needle with a warming tip and introducing a warming tip into tissue adjacent the plaque.

17. The method of claim 16, further comprising warming an adjacent tissue with the warming tip to thereby prevent a cooling injury to the adjacent tissue.

18. The method of claim 17, wherein warming is performed prior to cooling the plaque, contemporaneous with cooling the plaque, and/or after cooling the plaque.

19. The method of claim 18, wherein the warming tip is operatively coupled to the controller and the controller is configured to modulate warming the adjacent tissue.

20. The method of claim 18, wherein the warming the adjacent tissue is modulated in response to signals from a temperature sensor carried by the warming tip.

* * * * *